United States Patent [19]

Plath et al.

[11] Patent Number: 5,009,701

[45] Date of Patent: Apr. 23, 1991

[54] 5-(N-3,4,5,6-TETRAHYDROPHTHALIMIDO)-CINNAMIC ACID DERIVATIVES

[75] Inventors: Peter Plath, Frankenthal; Karl Eicken, Wachenheim; Lothar Rueb, Speyer; Barbara Schwalge, Ludwigshafen; Karl-Otto Westphalen, Speyer; Bruno Wuerzer, Otterstadt, all of Fed. Rep. of Germany

[73] Assignee: BASF Aktiengesellschaft, Ludwigshafen, Fed. Rep. of Germany

[21] Appl. No.: 403,382

[22] Filed: Sep. 6, 1989

[30] Foreign Application Priority Data

Sep. 9, 1988 [DE] Fed. Rep. of Germany ....... 3830733

[51] Int. Cl.$^5$ ................... A01N 43/38; C07D 209/48
[52] U.S. Cl. ......................................... 71/96; 548/513
[58] Field of Search .............................. 548/513; 71/96

[56] References Cited

U.S. PATENT DOCUMENTS

| 4,536,209 | 8/1985 | Jikihara et al. | 71/96 |
| 4,594,099 | 6/1986 | Yamada et al. | 71/96 |

FOREIGN PATENT DOCUMENTS

| 0049508 | 4/1982 | European Pat. Off. |
| 240659 | 10/1987 | European Pat. Off. |
| 3900353 | 9/1989 | Fed. Rep. of Germany |
| 61-27962 | 2/1986 | Japan |
| 2071100 | 9/1981 | United Kingdom |

OTHER PUBLICATIONS

JP 027 962/86 / Chem. Abstract.

Primary Examiner—Frederick E. Waddell
Assistant Examiner—Celia Chang
Attorney, Agent, or Firm—Keil & Weinkauf

[57] ABSTRACT 5-(N-3,4,5,6-Tetrahydrophthalimido)-cinnamic acid derivatives of the formula Ib

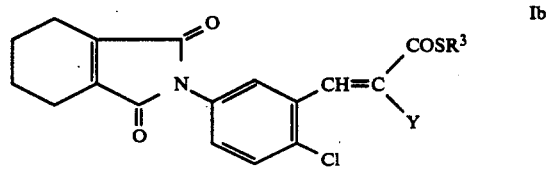

where the substituents have the following meanings:

Y is chlorine, bromine or $C_1-C_4$-alkyl;

$R^1$ is hydrogen, $C_1-C_8$-alkyl, substituted or unsubstituted $C_2-C_4$alkyl, $C_3-C_6$-alkenyl, $C_3-C_6$-alkynyl, or substituted or unsubstituted phenyl or benzyl, $R^2$ is $C_5-C_8$-alkyl, substituted or unsubstituted $C_2-C_4$-alkyl, $C_1-C_6$-alkoxy, $C_3-C_6$-alkenyl, $C_3-C_6$-alkenyloxy, $C_3-C_6$-alkynyl, $C_3-C_6$-alkynyloxy, or substituted or unsubstituted phenyl, phenoxy, benzyl or benzyloxy, $R_3$ $C_1-C_6$-alkyl, or substituted or unsubstituted $C_2-C_6$-alkyl, methods of manufacturing these compounds, and their use as herbicides.

12 Claims, No Drawings

5-(N-3,4,5,6-TETRAHYDROPHTHALIMIDO)CINNAMIC ACID DERIVATIVES

The present invention relates to 5-(N-3,4,5,6-tetrahydrophthalimido)cinnamic acid derivatives of the formulae Ia and Ib

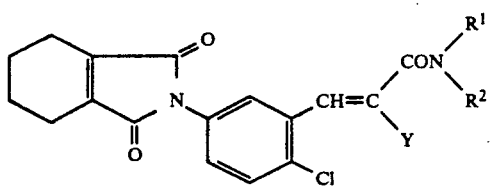

Ia

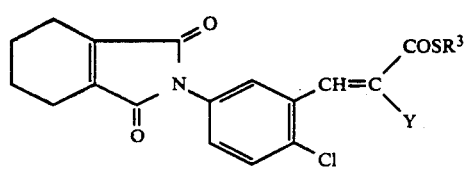

Ib where the substituents are defined as follows:

Y is chlorine, bromine or $C_1$–$C_4$-alkyl, $R^1$ is hydrogen, $C_1$–$C_8$-alkyl, $C_2$–$C_4$-alkyl which carries hydroxyl, $C_1$–$C_4$-alkoxy or $C_1$–$C_4$-alkylthio, $C_3$–$C_6$-alkenyl or, $C_3$–$C_6$-alkynyl, phenyl or benzyl, wherein the rings may carry from 1 to 3 of the following radicals: halogen, $C_1$–$C_4$-alkyl, $C_1$–$C_4$-alkoxy, $C_1$–$C_4$-haloalkyl, cyano, nitro, $C_1$–$C_4$-haloalkoxy, N-$C_1$–$C_4$-alkylamino, N,N-di-$C_1$–$C_4$-alkylamino and $C_1$–$C_4$-alkylthio, $R^2$ is $C_5$–$C_8$-alkyl, $C_2$–$C_4$-alkyl which carries hydroxyl, $C_1$–$C_4$-alkoxy or $C_1$–$C_4$-alkylthio, $C_1$–$C_6$-alkoxy, $C_3$–$C_6$-alkenyl, $C_3$–$C_6$-alkenyloxy, $C_3$–$C_6$-alkynyl, $C_3$–$C_6$-alkynyloxy or, phenyl, phenoxy, benzyl or benzyloxy, which radicals may carry from one to three of the following substituents: halogen, $C_1$–$C_4$-alkyl, $C_1$–$C_4$-alkoxy, $C_1$–$C_4$-alkylthio, $C_1$–$C_4$-haloalkyl, cyano, nitro, $C_1$–$C_4$-haloalkoxy, N-$C_1$–$C_4$-alkylamino and N,N-di-$C_1$–$C_4$-alkylamino and, $R^3$ is $C_1$–$C_6$-alkyl or, $C_2$–$C_6$-alkyl which may carry from one to three of the following substituents: $C_1$–$C_4$-alkoxy, $C_1$–$C_4$-alkylthio and hydroxyl, $R^1$ not being hydrogen when Y is chlorine or bromine.

The present invention further relates to processes for preparing these compounds and to the use thereof as herbicides.

Japanese Preliminary Published Application JP-A2-27,962/1986 discloses esters and amides of the structure I'

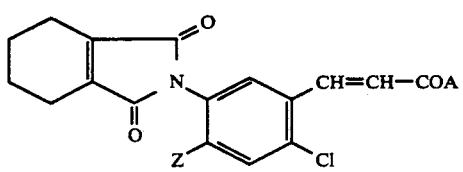

where A is for example —OCH$_3$, —NHCH$_3$, —N(CH$_3$)$_2$ or —N(CH$_2$CH=CH$_2$)$_2$ and Z is hydrogen or fluorine.

Furthermore, EP-A-240,659 describes compounds of the formula I''

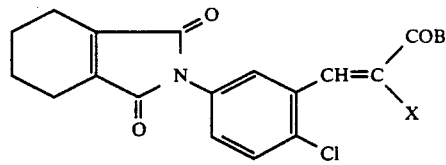

where B is inter alia NR$^4$R$^5$ where R$^4$ and R$^5$ are each for example independently of the other hydrogen and $C_1$–$C_4$-alkyl and X is for example hydrogen, —CH$_3$, —Cl or —Br.

However, the use close to crop plants in particular ideally requires compounds which combine lower application rate requirements with higher selectivity in respect of crop plants.

It is an object of the present invention to find and synthesize appropriate substances.

We have found that this object is achieved with the 5-(N-3,4,5,6-tetrahydrophthalimido)cinnamic acid derivatives of the formulae Ia and Ib defined at the beginning, which have an advantageous herbicidal effect in particular in postemergence and which are selective with respect to a number of crop plants.

We have also found processes for preparing compounds Ia and Ib.

Compounds Ia are obtained for example by reacting 3,4,5,6-tetrahydrophthalic anhydride with an equivalent amount of a 5-aminocinnamide of the formula V in an inert organic solvent:

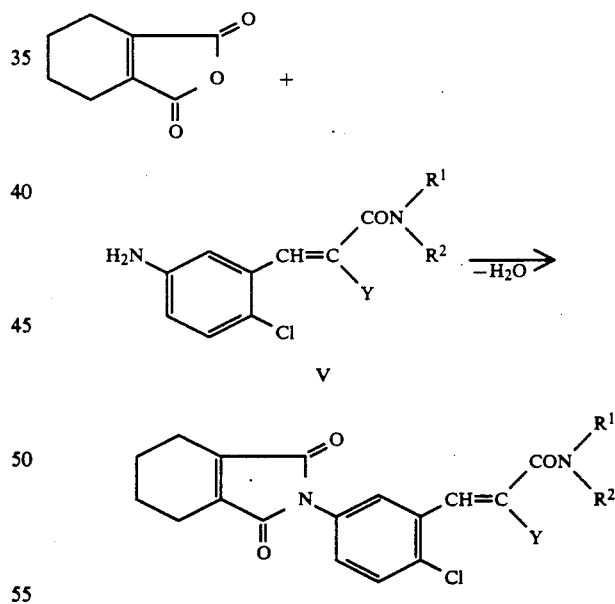

The solvent used is for example a lower alkanoic acid such as acetic acid, propionic acid or isobutyric acid, an ester thereof, such as ethyl acetate, a higher-boiling hydrocarbon, such as toluene or xylene, or dimethylformamide. The reaction generally takes place at from 25° C. to the boiling point of the particular reaction mixture, preferably at from 70° to 140° C. If an aprotic solvent is used, it is advisable to remove the water continuously.

The aniline derivatives of the formula V can be obtained in a conventional manner from the corresponding nitrophenyl derivatives IV either by reduction with inorganic compounds such as tin(II) salts or iron or, unless Y is bromine or chlorine, by catalytic hydrogenation over metal catalysts such as Raney nickel, palladium or platinum:

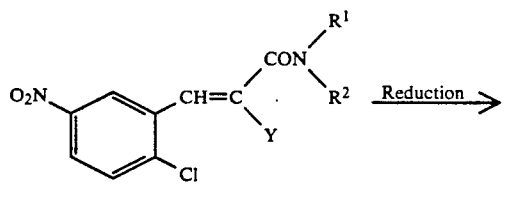

IV

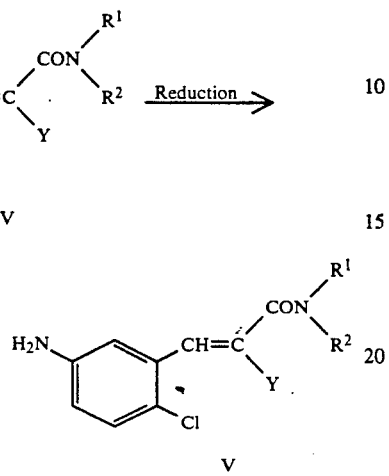

V

The nitrophenyl derivatives required are preparable in various ways, for example:

(a) If Y is $C_1$–$C_4$-alkyl, by reacting an appropriate nitrocinnamoyl chloride II (EP-A-240,659) in an inert organic solvent, which may contain water, with an amine III in the presence of a base:

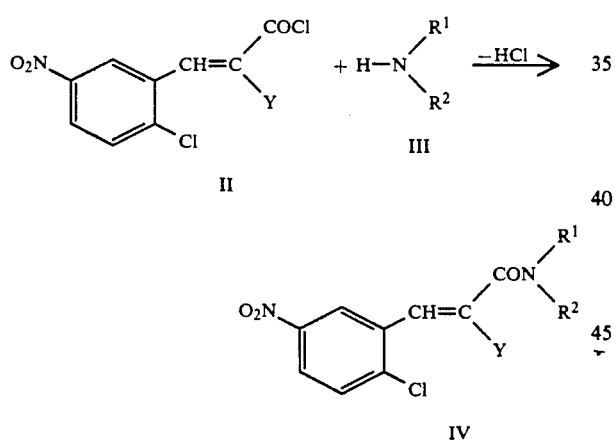

The reaction temperature is in general from −15° to +50° C., preferably from −10° to +40° C. Suitable solvents are for example tetrahydrofuran, dioxane, 1,2-dimethoxyethane and acetonitrile.

Suitable bases are inter alia the amine itself in excess and tertiary amines such as triethylamine, diisopropylethylamine, N,N-dimethyl-p-aminopyridine, N-methylpyrrolidine, N,N,N',N'-tetramethylethylenediamine, 1,5-diazabicyclo[4.3.0]non-5-ene and 1,8-diazabicyclo[5.4.0]-undec-7-ene.

It is preferable to carry out the reaction in tetrahydrofuran or dioxane, in which case the amine can be added as an aqueous solution or as a solution in one of the abovementioned ethers, and with triethylamine as the base.

(b) If Y is chlorine or bromine (Hal), by reacting a nitrocinnamide of the formula IVa in an inert organic solvent with the appropriate halogen:

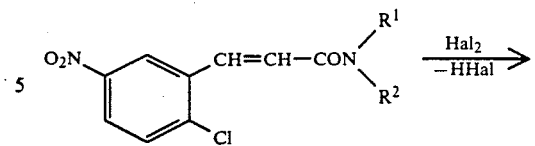

IVa

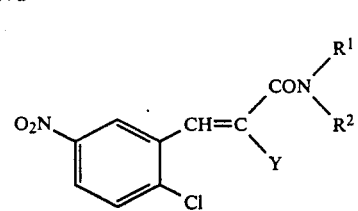

IV

The reaction is in general carried out at from 0° to 60° C., preferably from 15° to 40° C.

Suitable solvents are for example methylene chloride, chloroform, carbon tetrachloride, 1,1,1-trichloroethane and chlorobenzene, of which methylene chloride, chloroform and 1,1,1-trichloroethane are preferred.

The compounds of the formulae Ia and Ib are obtained for example from the corresponding 5-(N-3,4,5,6-tetrahydrophthalimido)cinnamoyl chlorides VI by reaction with a mercaptan VII or an amine III, for example as follows:

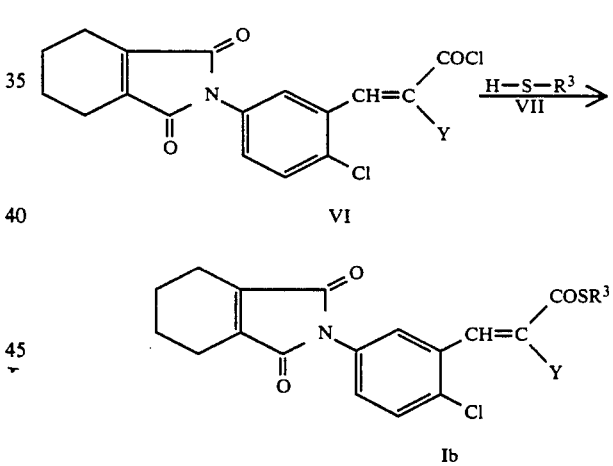

The reaction is carried out in a conventional manner, in general in an inert organic solvent in the presence of a base at from −15° to +50° C., preferably at from −5° to +30° C.

Suitable solvents for this reaction are inter alia hydrocarbons such as toluene and xylene, lower esters of alkanoic acids such as ethyl acetate and ethers such as tetrahydrofuran, dioxane and diisopropyl ether.

Suitable auxiliary bases are for example tertiary amines such as those mentioned above and also pyridine, collidine and methylpiperidine, but preferably triethylamine.

A synthesis for cinnamoyl chloride VI is described for example in EP-A-240,659.

With a view to the intended use of compounds Ia and Ib, the following radicals come into consideration as substituents:

Y is chlorine; bromine; alkyl such as methyl, ethyl, n-propyl, isopropyl, n-butyl, isobutyl, sec-butyl or tert-butyl, preferably methyl or ethyl;

$R^1$ is hydrogen; phenyl; benzyl; alkyl such as mentioned under Y and also n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular methyl or ethyl, alkenyl such as allyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-ethyl-2-propenyl, 2-hexenyl, 3-hexenyl, 4-hexenyl, 5-hexenyl, 1-methyl-2-hexenyl, 2-methyl-2-pentenyl, 3-methyl-2-pentenyl, 4-methyl-2-pentenyl, 5-methyl-2-pentenyl, 1-ethyl-2-butenyl, 2-ethyl-2-butenyl, 1-ethyl-1-methyl-2-propenyl or 1-ethyl-2-methyl-2-propenyl, in particular allyl, alkynyl such as propyn-2-yl, butyn-2-yl, butyn-3-yl, 1-methylpropyn-2-yl, pentyn-2-yl, pentyn-3-yl, pentyn-4-yl, 1-methylbutyn-2-yl, 1-methylbutyn-3-yl, 2-methylbutyn-3-yl, 1,1-dimethylpropyn-2-yl, 1-ethylpropyn-2-yl, hexyn-2-yl, hexyn-3-yl, hexyn-4-yl, hexyn-5-yl, 1-methylpentyn-2-yl, 4-methylpentyn-2-yl, 5-methylpentyn-2-yl, 1,1-dimethylbutyn-2-yl, 1-ethylbutyn-2-yl or 1-ethyl-1-methylpropyn-2-yl, in particular propyn-2-yl.

Of the radicals $R^1$, the $C_2-C_4$-alkyl, phenyl and benzyl radicals may in turn carry the following substituents:

hydroxyl;

alkoxy such as methoxy, ethoxy, n-propyloxy, isopropyloxy, n-butyloxy, isobutyloxy or tert-butoxy in the 2-, 3- or 4-position of the alkyl radical, in particular methoxy, ethoxy or isopropyloxy in the 2-, 3- or 4-position of the alkyl radical;

alkylthio such as methylthio, ethylthio, n-propylthio, isopropylthio, n-butylthio, isobutylthio or tert-butylthio in the 2-, 3- or 4-position of the alkyl radical, in particular methylthio or ethylthio in the 2-position of the alkyl radical.

If $R^1$ is phenyl or benzyl, the following substituents also come into consideration:

cyano; nitro; halogen atoms such as fluorine, chlorine or bromine, preferably chlorine; alkyl, alkoxy, alkylthio or haloalkyl as mentioned above and also alkylamino and dialkylamino such as methylamino, dimethylamino, ethylamino, methylethylamino, diethylamino, n-propylamino, N-methyl-N-propylamino, N-ethyl-N-propylamino, N,N-dipropylamino and N,N-diisopropylamino, in particular N,N-dimethylamino, $R^1$ not being hydrogen when Y is chlorine or bromine.

$R^2$ is $C_5-C_8$-alkyl as mentioned under $R^1$; alkoxy such as methoxy, ethoxy, n-propyloxy, isopropyloxy and the isomeric butoxy, pentyloxy and hexyloxy groups, in particular methoxy or ethoxy; alkenyloxy such as 2-propenyloxy, 2-butenyloxy, 3-butenyloxy, 1-methyl-2-propenyloxy, 2-methyl-2-propenyloxy, 2-pentenyloxy, 1-methyl-2-butenyloxy, 2-methyl-2-butenyloxy, 3-methyl-2-butenyloxy or 1-ethyl-2-propenyloxy, in particular 2-propenyloxy or 2-butenyloxy; and alkynyloxy such as 2-propynyloxy, 2-butynyloxy, 3-butynyloxy, 1-methyl-2-propynyloxy, 2-pentynyloxy, 1-methyl-2-butynyloxy, 1,1-dimethyl-2-propynyloxy, 1-ethyl-2-propynyloxy or 2-pentynyloxy, in particular 2-propynyloxy, 2-butynyloxy or 3-butynyloxy.

$R^3$ is unsubstituted $C_1-C_6$-alkyl as defined under $R^1$ or one of the abovementioned $C_2-C_6$-alkyl groups which may be substituted, preferably monosubstituted, by the abovementioned alkoxy or alkylthio radicals or by hydroxyl.

Examples of very active compounds Ia and Ib are given below in Tables 1 and 2.

TABLE 1

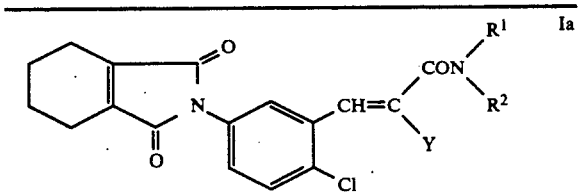

| Y | $R^1$ | $R^2$ |
|---|---|---|
| CH₃ | H | (CH₂)₄CH₃ |
| CH₃ | H | CH₂CH(CH₃)(CH₂)₂CH₃ |
| CH₃ | H | (CH₂)₂CH(CH₃)₂ |
| CH₃ | H | CH₂CH(CH₂CH₃)₂ |
| CH₃ | H | CH(CH₃)CH(CH₃)₂ |
| CH₃ | H | CH₂C(CH₃)₃ |
| CH₃ | H | CH₂CH=CH₂ |
| CH₃ | H | CH₂C(CH₃)=CH₂ |
| CH₃ | H | CH₂CH=CHCH₃ |
| CH₃ | H | CH₂C≡CH |
| CH₃ | H | CH(CH₃)C≡CH |
| CH₃ | H | CH₂C≡CCH₃ |
| CH₃ | H | CH₂Ph |
| CH₃ | H | (CH₂)₂OCH₃ |
| CH₃ | H | (CH₂)₂OCH₂CH₃ |
| CH₃ | H | CH₂CH(CH₃)OCH₃ |
| CH₃ | H | CH(CH₃)CH₂OCH₃ |
| CH₃ | H | CH(CH₂CH₃)CH₂OCH₃ |
| CH₃ | H | CH(CH₂OCH₃)(CH₂)₂OCH₃ |
| CH₃ | H | (CH₂)₂SCH₃ |
| CH₃ | H | (CH₂)₂SCH₂CH₃ |
| CH₃ | H | OCH₃ |
| CH₃ | H | OCH₂CH₃ |
| CH₃ | H | OCH₂CH=CH₂ |
| CH₃ | H | OCH₂C(CH₃)=CH₂ |
| CH₃ | H | OCH₂C≡CH |
| CH₃ | H | Ph |
| CH₃ | H | 2-F—C₆H₄ |
| CH₃ | H | 2-Cl—C₆H₄ |
| CH₃ | H | 2-CH₃—C₆H₄ |
| CH₃ | H | 2-OCH₃—C₆H₄ |
| CH₃ | H | 3-Cl—C₆H₄ |
| CH₃ | H | 4-Cl—C₆H₄ |
| CH₃ | H | 3-CH₃—C₆H₄ |
| CH₃ | H | 4-OCH₃—C₆H₄ |
| CH₃ | H | 2,4-Cl,Cl—C₆H₃ |
| CH₃ | H | 2-Cl,4-CH₃—C₆H₃ |
| CH₃ | H | 2-Cl,6-CH₃—C₆H₃ |
| CH₃ | H | 3-CF₃—C₆H₄ |
| CH₃ | H | 4-CN-C₆H₄ |
| CH₃ | H | 3-NO₂—C₆H₄ |
| CH₃ | H | 2-SCH₃—C₆H₄ |
| CH₃ | H | 4-N(CH₃)₂—C₆H₄ |
| CH₂CH₃ | H | (CH₂)₄CH₃ |
| CH₂CH₃ | H | (CH₂)₂CH(CH₃)₂ |
| CH₂CH₃ | H | CH₂CH=CH₂ |
| CH₂CH₃ | H | CH₂C≡CH |
| CH₂CH₃ | H | CH₂Ph |
| CH₂CH₃ | H | Ph |
| CH₂CH₃ | H | 2-Cl-Ph |
| CH₂CH₃ | H | (CH₂)₂OH |
| CH₂CH₃ | H | (CH₂)₂OCH₃ |
| CH₂CH₃ | H | (CH₂)₂SCH₃ |
| CH₂CH₃ | H | OCH₃ |
| CH₂CH₃ | H | OCH₂CH=CH₂ |
| CH₂CH₃ | H | OCH₂C≡CH |
| Cl | CH₃ | (CH₂)₄CH₃ |
| Cl | CH₃ | (CH₂)₂CH(CH₃)₂ |

TABLE 1-continued

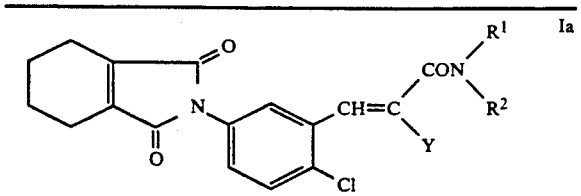

| Y | R¹ | R² |
|---|---|---|
| Cl | CH₃ | CH₂CH=CH₂ |
| Cl | CH₃ | CH₂C≡CH |
| Cl | CH₃ | CH₂Ph |
| Cl | CH₃ | Ph |
| Cl | CH₃ | 2-Cl-Ph |
| Cl | CH₃ | (CH₂)₂OH |
| Cl | CH₃ | (CH₂)₂OCH₃ |
| Cl | CH₃ | (CH₂)₂SCH₃ |
| Cl | CH₃ | OCH₃ |
| Cl | CH₃ | OCH₂CH=CH₂ |
| Cl | CH₃ | OCH₂C≡CH |
| Br | CH₃ | (CH₂)₄CH₃ |
| Br | CH₃ | (CH₂)₂CH(CH₃)₂ |
| Br | CH₃ | CH₂CH=CH₂ |
| Br | CH₃ | CH₂C≡CH |
| Br | CH₃ | CH₂Ph |
| Br | CH₃ | Ph |
| Br | CH₃ | 2-Cl-Ph |
| Br | CH₃ | (CH₂)₂OH |
| Br | CH₃ | (CH₂)₂OCH₃ |
| Br | CH₃ | (CH₂)₂SCH₃ |
| Br | CH₃ | OCH₃ |
| Br | CH₃ | OCH₂CH=CH₂ |
| Br | CH₃ | OCH₂C≡CH |
| CH₃ | CH₃ | (CH₂)₄CH₃ |
| CH₃ | CH₃ | (CH₂)₂CH(CH₃)₂ |
| CH₃ | CH₃ | CH₂CH=CH₂ |
| CH₃ | CH₃ | CH₂C≡CH |
| CH₃ | CH₃ | CH₂Ph |
| CH₃ | CH₃ | Ph |
| CH₃ | CH₃ | 2-Cl-Ph |
| CH₃ | CH₃ | (CH₂)₂OH |
| CH₃ | CH₃ | (CH₂)₂OCH₃ |
| CH₃ | CH₃ | (CH₂)₂SCH₃ |
| CH₃ | CH₃ | OCH₃ |
| CH₃ | CH₃ | OCH₂CH=CH₂ |
| CH₃ | CH₃ | OCH₂C≡CH |
| CH₃ | CH₂CH₃ | (CH₂)₄CH₃ |
| CH₃ | CH₂CH₃ | (CH₂)₂CH(CH₃)₂ |
| CH₃ | CH₂CH₃ | CH₂CH=CH₂ |
| CH₃ | CH₂CH₃ | CH₂C≡CH |
| CH₃ | CH₂CH₃ | CH₂Ph |
| CH₃ | CH₂CH₃ | Ph |
| CH₃ | CH₂CH₃ | 2-Cl-Ph |
| CH₃ | CH₂CH₃ | (CH₂)₂OH |
| CH₃ | CH₂CH₃ | (CH₂)₂OCH₃ |
| CH₃ | CH₂CH₃ | (CH₂)₂SCH₃ |
| CH₃ | CH₂CH₃ | OCH₃ |
| CH₃ | CH₂CH₃ | OCH₂CH=CH₂ |
| CH₃ | CH₂CH₃ | OCH₂C≡CH |
| CH₃ | CH(CH₃)₂ | (CH₂)₄CH₃ |
| CH₃ | CH(CH₃)₂ | (CH₂)₂CH(CH₃)₂ |
| CH₃ | CH(CH₃)₂ | CH₂CH=CH₂ |
| CH₃ | CH(CH₃)₂ | CH₂C≡CH |
| CH₃ | CH(CH₃)₂ | CH₂Ph |
| CH₃ | CH(CH₃)₂ | Ph |
| CH₃ | CH(CH₃)₂ | 2-Cl-Ph |
| CH₃ | CH(CH₃)₂ | (CH₂)₂OH |
| CH₃ | CH(CH₃)₂ | (CH₂)₂OCH₃ |
| CH₃ | CH(CH₃)₂ | (CH₂)₂SCH₃ |
| CH₃ | CH(CH₃)₂ | OCH₃ |
| CH₃ | CH(CH₃)₂ | OCH₂CH=CH₂ |
| CH₃ | CH(CH₃)₂ | OCH₂C≡CH |
| CH₃ | CH₂CH=CH₂ | (CH₂)₄CH₃ |
| CH₃ | CH₂CH=CH₂ | (CH₂)₂CH(CH₃)₂ |
| CH₃ | CH₂CH=CH₂ | CH₂CH=CH₂ |
| CH₃ | CH₂CH=CH₂ | CH₂C≡CH |
| CH₃ | CH₂CH=CH₂ | CH₂Ph |
| CH₃ | CH₂CH=CH₂ | Ph |
| CH₃ | CH₂CH=CH₂ | 2-Cl-Ph |
| CH₃ | CH₂CH=CH₂ | (CH₂)₂OH |

TABLE 1-continued

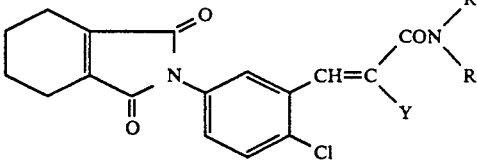

| Y | R¹ | R² |
|---|---|---|
| CH₃ | CH₂CH=CH₂ | (CH₂)₂OCH₃ |
| CH₃ | CH₂CH=CH₂ | (CH₂)₂SCH₃ |
| CH₃ | CH₂CH=CH₂ | OCH₃ |
| CH₃ | CH₂CH=CH₂ | OCH₂CH=CH₂ |
| CH₃ | CH₂CH=CH₂ | OCH₂C≡CH |
| CH₃ | CH₂C≡CH | (CH₂)₄CH₃ |
| CH₃ | CH₂C≡CH | (CH₂)₂CH(CH₃)₂ |
| CH₃ | CH₂C≡CH | CH₂CH=CH₂ |
| CH₃ | CH₂C≡CH | CH₂C≡CH |
| CH₃ | CH₂C≡CH | CH₂Ph |
| CH₃ | CH₂C≡CH | Ph |
| CH₃ | CH₂C≡CH | 2-Cl-Ph |
| CH₃ | CH₂C≡CH | (CH₂)₂OH |
| CH₃ | CH₂C≡CH | (CH₂)₂OCH₃ |
| CH₃ | CH₂C≡CH | (CH₂)₂SCH₃ |
| CH₃ | CH₂C≡CH | OCH₃ |
| CH₃ | CH₂C≡CH | OCH₂CH=CH₂ |
| CH₃ | CH₂C≡CH | OCH₂C≡CH |
| CH₃ | (CH₂)₂OCH₃ | (CH₂)₄CH₃ |
| CH₃ | (CH₂)₂OCH₃ | (CH₂)₂CH(CH₃)₂ |
| CH₃ | (CH₂)₂OCH₃ | CH₂CH=CH₂ |
| CH₃ | (CH₂)₂OCH₃ | CH₂C≡CH |
| CH₃ | (CH₂)₂OCH₃ | CH₂Ph |
| CH₃ | (CH₂)₂OCH₃ | Ph |
| CH₃ | (CH₂)₂OCH₃ | 2-Cl-Ph |
| CH₃ | (CH₂)₂OCH₃ | (CH₂)₂OH |
| CH₃ | (CH₂)₂OCH₃ | (CH₂)₂OCH₃ |
| CH₃ | (CH₂)₂OCH₃ | (CH₂)₂SCH₃ |
| CH₃ | (CH₂)₂OCH₃ | OCH₃ |
| CH₃ | (CH₂)₂OCH₃ | OCH₂CH=CH₂ |
| CH₃ | (CH₂)₂OCH₃ | OCH₂C≡CH |

TABLE 2

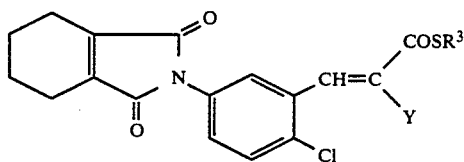

| Y | R³ |
|---|---|
| CH₃ | CH₃ |
| CH₃ | CH₂CH₃ |
| CH₃ | (CH₂)₂CH₃ |
| CH₃ | CH(CH₃)₂ |
| CH₃ | CH₂CH(CH₃)₂ |
| CH₃ | C(CH₃)₃ |
| CH₃ | (CH₂)₂OCH₃ |
| CH₃ | (CH₂)₂SCH₃ |
| CH₃ | (CH₂)₂OH |
| CH₂CH₃ | CH₃ |
| CH₂CH₃ | CH₂CH₃ |
| CH₂CH₃ | (CH₂)₂CH₃ |
| CH₂CH₃ | CH(CH₃)₂ |
| CH₂CH₃ | CH₂CH(CH₃)₂ |
| CH₂CH₃ | C(CH₃)₃ |
| CH₂CH₃ | (CH₂)₂OCH₃ |
| CH₂CH₃ | (CH₂)₂SCH₃ |
| CH₂CH₃ | (CH₂)₂OH |
| Cl | CH₃ |
| Cl | CH₂CH₃ |
| Cl | (CH₂)₂CH₃ |
| Cl | CH(CH₃)₂ |
| Cl | CH₂CH(CH₃)₂ |
| Cl | C(CH₃)₃ |
| Cl | (CH₂)₂OCH₃ |
| Cl | (CH₂)₂SCH₃ |

TABLE 2-continued

Ib: structure showing cyclohexene fused to a dicarbonyl-N ring, N attached to phenyl bearing CH=C(COSR³)(Y) and Cl substituents.

| Y | R³ |
|---|---|
| Cl | (CH₂)₂OH |
| Br | CH₃ |
| Br | CH₂CH₃ |
| Br | (CH₂)₂CH₃ |
| Br | CH(CH₃)₂ |
| Br | CH₂CH(CH₃)₂ |
| Br | C(CH₃)₃ |
| Br | (CH₂)₂OCH₃ |
| Br | (CH₂)₂SCH₃ |
| Br | (CH₂)₂OH |

The 5-(N-3,4,5,6-tetrahydrophthalimido)-cinnamic acid derivatives Ia and Ib, and herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, alkali metal and alkaline earth metal salts of dibutylnaphthalenesulfonic acid, lauryl ether sulfate, fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient. The active ingredients are used in a purity of from 90 to 100, and preferably from 95 to 100, % (according to the NMR spectrum).

The compounds Ia and b according to the invention may be formulated for example as follows.

I. 90 parts by weight of compound no. 1.001 is mixed with 10 parts by weight of N-methyl-alpha-pyrrolidone. A mixture is obtained which is suitable for application in the form of very fine drops.

II. 20 parts by weight of compound no. 1.008 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1.003 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 2.010 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 2.001 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 2.007 is intimately mixed with 97 parts by weight of particulate kaolin. A dust is obtained containing 3% by weight of the active ingredient.

VII. 30 parts by weight of compound no. 1.015 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 2.006 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 5.0, preferably 0.01 to 1.0, kg of active ingredient per hectare.

In view of the number of application methods possible, the compounds according to the invention, or agents containing them, may be used in a further large number of crops for removing unwanted plants. The following crops are given by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Triticum durum | durum wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the 5-(N-3,4,5,6-tetrahydrophthalimido)-cinnamic acid derivatives of the formulae Ia and Ib may be mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, aryloxy- or heteroaryloxyphenylpropionic acids and salts, esters and amides thereof, etc.

It may also be useful to apply the novel compounds Ia and b, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

SYNTHESIS EXAMPLES

The directions given in the synthesis examples below were used, after appropriate modifications of the starting materials, to obtain further compounds Ia and b. The compounds thus obtained are listed with physical data in the tables below.

EXAMPLE 1

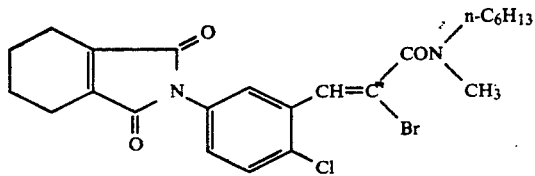

(a) At 0° to 5° C., 11.5 g (0.10 mol) of N-methylhexylamine in 100 ml of tetrahydrofuran was added to a solution of 12.3 g (0.05 mol) of 2-chloro5-nitrocinnamyl chloride in 40 ml of tetrahydrofuran. After the mixture had been stirred for 2 hours, the solvent was removed, and the residue thus obtained was dissolved in ethyl acetate and extracted with 5% strength sodium hydroxide solution. The organic phase was washed with water, followed by separation and drying, to give 13.3 g (81% of theory) of 2-chloro-5-nitrocinnamic acid-N-methyl-N-hexylamide.

(b) At 25° C., 6.4 g (0.04 mol) of bromine in 10 ml of 1,1,1-trichloroethane was added to 120 g (0.037 mol) of the compound obtained under (a) in 100 ml of 1,1,1-trichloroethane. After the mixture had been stirred for 1 hour at 40° C. a further 0.5 ml of bromine was added and the mixture left at 40° C. for a further hour. The solvent was then distilled off and the residue triturated with petroleum ether.

The crystals thus obtained were dissolved in 150 ml of methanol and, at 25° C., 8.0 g (0.045 mol) of a 30% strength sodium methylate solution in 80 ml of methanol was added dropwise. After 2 hours at 65° C. the solvent was removed and the residue was stirred with water and extracted with ethyl acetate. The organic phase was washed, dried and concentrated to give 11.8 g (79%) of crude 2-chloro-5-nitro-α-bromocinnamic acid-N-methyl-N-hexylamide which was reacted without further purification.

(c) 11.0 g (0.049 mol) of the nitro compound obtained under (b) was added in portions to a suspension of 8.1 g (0.145 mol) of iron powder in a mixture, heated to 60° C., of 80 ml of methanol and 40 ml of glacial acetic acid, and the mixture was heated for 2 hours at 80° C. Upon completion of the reaction, the mixture was stirred into water, the solid was filtered off and the aqueous phase was extracted with ethyl acetate. The organic phase was washed, dried and concentrated to give 10.2 g (100%) of 2-chloro-5-amino-α-bromocinnamic acid-N-methyl-N-hexylamide as an oil which was reacted without further purification.

(d) A mixture of 10.2 g (0.027 mol) of the aniline obtained under (c) and 4.1 g (0.027 mol) of tetrahydrophthalic anhydride in 80 ml of glacial acetic acid was boiled for 3 hours. Upon completion of the reaction the mixture was stirred into water and extracted with ethyl acetate. The organic phase was washed, dried and concentrated to give 7.1 g (52% of theory) of 5-(N-3,4,5,6-tetrahydrophthalimido)-2-chloro-α-bromocinnamic acid-N'-methyl-N'-hexylamide (active ingredient no. 1.028) as an oil.

EXAMPLE 2

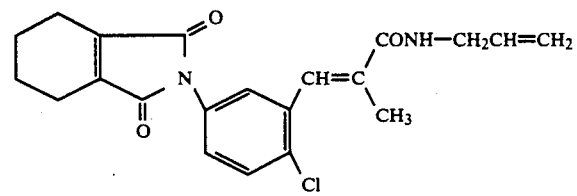

(a) At 5° to 10° C., 10.4 g (0.04 mol) of 2-chloro-5-nitro-α-methylcinnamyl chloride in 100 ml of tetrahydrofuran was added to 4.6 g (0.08 mol) of alkylamine in 50 ml of tetrahydrofuran. After 2 hours the solvent was stripped off, and the remaining mixture was stirred into water. The solid which formed was isolated. Drying of the solid gave 8.1 g (81% of theory) of 2-chloro-5-nitro-α-methylcinnamic acid-N-allylamide of m.p. 111°–112° C.

(b) Analogously to 1(c), 9.1 g (0.032 mol) of the nitro compound obtained under (a) and 9.1 g (0.162 mol) of iron powder in 150 ml of methanol and 100 ml of glacial acetic acid were worked up to give 8.1 g (100% of theory) of 5-amino-2-chloro-α-methylcinnamic acid-N-allylamide as an oil.

(c) Analogously to 1(d), 8.1 g (0.032 mol) of the amine obtained under (b) and 4.9 g (0.032 mol) of tetrahydrophthalic anhydride in 100 ml of glacial acetic acid were worked up to give 9.2 g (74% of theory) of 5-(N-3,4,5,6-tetrahydrophthalimido)-2-chloro-α-methylcinnamic acid-N-allylamide of m.p. 89°–90° C. (active ingredient no. 1.007).

EXAMPLE 3

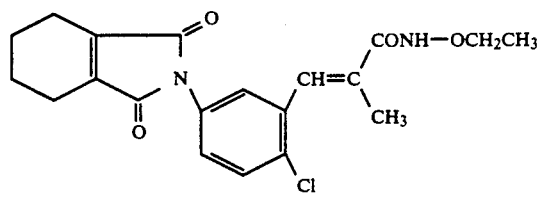

(a) At 25° C., 5.9 g (0.06 mol) of O-ethylhydroxylamine hydrochloride in 100 ml of tetrahydrofuran and then, at 0° to 5° C., 10.9 g (0.03 mol) of 5-(N-3,4,5,6-tetrahydrophthalimido)-2-chloro-α-methylcinnamyl chloride in 50 ml of tetrahydrofuran were added to 10.8 g (0.06 mol) of a 30% strength sodium methylate solution in methanol. After 4 hours at 25° C., the reaction mixture was concentrated and the residue was stirred with water and extracted with ethyl acetate. The organic phase was washed, dried and concentrated, and the residue was triturated with petroleum ether to give 10.0 g (86% of theory) of 5-(N-3,4,5,6-tetrahydrophthalimido)-2-chloro-α-methylcinnamic acid-N'-ethoxyamide of m.p. 83°–84° C. (active ingredient no. 1.016).

EXAMPLE 4

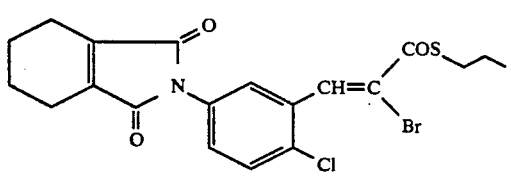

(a) At 65° C., 120.3 g (0.28 mol) of methyl 5-(N-3,4,5,6-tetrahydrophthalimido)-2-chloro-α-bromocinnamate (EP No. 240,659) was added to a mixture of 330 ml of water, 170 ml of methanol and 40 g (1 mol) of sodium hydroxide, and the whole was brought to the boil. After 7 minutes the mixture was allowed to cool to 40° C., and was then introduced into 250 ml of 10% strength hydrochloric acid and extracted twice with 250 ml of ethyl acetate. The organic phase was separated and dried, and the solvent was stripped off under reduced pressure. The oily residue was crystallized with glacial acetic acid/water and dried, giving 5-(N-3,4,5,6-tetrahydrophthalimido)-2-chloro-α-bromocinnamic acid; m.p. 90° C.

(b) 118 g (0.28 mol) of the acid prepared under (a) was dissolved in 400 ml of toluene; 6 drops of dimethylformamide were added and the mixture was heated to 80° C. Subsequently, 107 g (0.9 mol) of thionyl chloride was added and the mixture was boiled for 5 hours. The solvent was distilled off under reduced pressure to give 89 g of crude 5-(N-3,4,5,6-tetrahydrophthalimido)-2-chloro-α-bromocinnamyl chloride as an oil.

(c) At 25° to 30° C., 12.9 g (0.03 mol) of the acid chloride prepared under (b) in 150 ml of ethyl acetate was added to a solution of 2.3 g (0.03 mol) of n-propylmercaptan and 3.5 g (0.035 mol) of triethylamine in 50 ml of ethyl acetate. The mixture was stirred for 3 hours at 25° to 30° C. and then extracted with 50 ml of 5% strength sodium hydroxide solution. The organic phase was washed with water and dried, and the solvent was distilled off to give 10.3 g of 5-(N-3,4,5,6-tetrahydrophthalimido)-2-chloro-α-bromocinnamic acid-n-propylthio ester as an oil (active ingredient no. 2.003, Table 4).

TABLE 3

| No. | Y | $R^1$ | $R^2$ | mp °C. |
|---|---|---|---|---|
| 1.001 | $CH_3$ | H | 3-methyl-butyl-2 | 122–123 |
| 1.002 | $CH_3$ | H | neopentyl | 123–124 |
| 1.003 | $CH_3$ | H | isoamyl | 88–89 |
| 1.004 | $CH_3$ | H | 2-ethylbutyl | 117–118 |
| 1.005 | $CH_3$ | H | n-pentyl | 87–88 |
| 1.006 | $CH_3$ | H | 2-methylpentyl | 68–69 |
| 1.007 | $CH_3$ | H | allyl | 89–90 |
| 1.008 | $CH_3$ | H | 2-methylallyl | 70–71 |
| 1.009 | $C_2H_5$ | H | allyl | 117–118 |
| 1.010 | $CH_3$ | H | 2-methoxyethyl | 99–100 |
| 1.011 | $CH_3$ | H | 2-methyl-thioethyl | oil |
| 1.012 | $CH_3$ | H | 3-methoxypropyl-2 | 70–71 |
| 1.013 | $CH_3$ | H | 1-methoxybutyl-2 | 98–99 |
| 1.014 | $CH_3$ | H | 4-methoxybutyl-2 | oil |
| 1.015 | $CH_3$ | $CH_2CH_2OCH_3$ | $CH_2CH_2OCH_3$ | 59–61 |
| 1.016 | $CH_3$ | H | ethoxy | 83–84 |
| 1.017 | $CH_3$ | H | allyloxy | 120–121 |
| 1.018 | $CH_3$ | $CH_3$ | methoxy | 99–101 |
| 1.019 | $C_2H_5$ | H | phenyl | 179–180 |
| 1.020 | $CH_3$ | H | 2-Cl-phenyl | 159–160 |
| 1.021 | $CH_3$ | H | 3-Cl-phenyl | 176–178 |
| 1.022 | $CH_3$ | H | 4-Cl-phenyl | 128–130 |
| 1.023 | $CH_3$ | H | 2-$CH_3$-phenyl | 104–105 |
| 1.024 | $CH_3$ | H | 3-$CH_3$-phenyl | 172–173 |
| 1.025 | $CH_3$ | H | 2-$CH_3O$-phenyl | 204–205 |
| 1.026 | $CH_3$ | H | 2-Cl,6-$CH_3$-phenyl | 167–168 |
| 1.027 | $CH_3$ | H | 2,6-Cl,Cl-phenyl | 186–187 |
| 1.028 | Br | $CH_3$ | n-hexyl | oil |

TABLE 4

| No. | Y | $R^3$ | mp (°C.) |
|---|---|---|---|
| 2.001 | $CH_3$ | $CH_3$ | 135–136 |
| 2.002 | $CH_3$ | $C_2H_5$ | 105–106 |
| 2.003 | $CH_3$ | n-$C_3H_7$ | 80–82 |
| 2.004 | $CH_3$ | n-$C_4H_9$ | 75–77 |
| 2.005 | $CH_3$ | i-$C_4H_9$ | 86–87 |
| 2.006 | $CH_3$ | $CH_2CH_2OH$ | 77–79 |
| 2.007 | Br | $CH_3$ | oil |
| 2.008 | Br | $C_2H_5$ | oil |
| 2.009 | Br | n-$C_3H_7$ | oil |
| 2.010 | Br | i-$C_3H_7$ | oil |
| 2.011 | Br | $CH_2CH_2OH$ | 70–72 |
| 2.012 | Br | $CH_2CH_2OCH_3$ | oil |

USE EXAMPLES

The action of the 5-(N-3,4,5,6-tetrahydrophthalimido)-cinnamic acid derivatives Ia and Ib on the growth of test plants was examined in the following greenhouse experiments.

The vessels employed were plastic flowerpots having a volume of 300 cm³ and filled with a sandy loam containing about 3.0% humus. The seeds of the test plants were sown separately, according to species.

For the postemergence treatment, the plants were grown, depending on growth form, to a height of 3 to 15 cm before being treated. In this treatment method, either plants which had been sown in the pots and grown there were selected, or they were cultivated separately as seedlings and transplanted to the pots a few days before being treated with the compounds suspended or emulsified in water by spraying them through finely distributing nozzles. The application rates for postemergence treatment were 0.015 to 0.03 kg/ha.

The pots were set up in the greenhouse, species from warmer climates in warmer areas (20° to 35° C.) and species from moderate climates at 10° to 20° C. The experiments were run for from 2 to 4 weeks. During this time the plants were tended and their reactions to the various treatments assessed. The assessment scale was 0 to 100, 100 denoting nonemergence or complete destruction of at least the visible plant parts, and 0 denoting no damage or normal growth.

Active ingredients nos. 1.005 and 2.002, applied postemergence at rates of 0.015 and 0.03 kg/ha, combated unwanted broadleaved plants excellently.

Active ingredients nos. 1.006 and 1.008, applied postemergence at a rate of 0.03 kg/ha, combated unwanted broadleaved plants very well without causing any appreciable damage to wheat as an example of a crop plant.

The plants used in these greenhouse experiments were *Abutilon theophrasti, Amaranthus retroflexus, Chrysanthemum corinarium, Euphorbia heterophylla, Galium aparine, Lamium amplexicaule, Malva neglecta, Mercurialis annua, Oryza sativa, Solanum nigrum* and *Triticum aestivum*.

We claim:

1. A 5-(N-3,4,5,6-tetrahydrophthalimido)cinnamic acid compound of the formula Ib

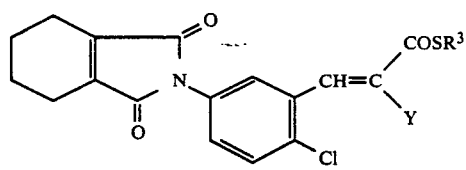

where the substituents have the following meanings:

Y is chlorine, bromine or $C_1$–$C_4$-alkyl, and $R^3$ is $C_1$–$C_6$-alkyl, or $C_2$–$C_6$-alkyl mono- to tri-substituted by $C_1$–$C_4$-alkoxy, $C_1$–$C_4$-alkylthio and/or hydroxyl.

2. A herbicidal composition which comprises: an effective amount of a 5-(N-3,4,5,6-tetrahydrophthalimido)-cinnamic acid compound of the formula Ib as set forth in claim 1, and herbicidally acceptable carrier.

3. A process for combating the growth of unwanted plants, wherein the unwanted plants and/or their habitat are treated with a herbicidally effective amount of a 5-(N-3,4,5,6-tetrahydrophthalimido)-cinnamic acid compound Ib as set forth in claim 1.

4. A compound of the formula Ib as defined in claim 1, wherein Y is $CH_3$ and $R^3$ is $CH_3$.

5. A herbicidal composition as defined in claim 2, wherein in the active compound of the formula Ib, Y is $CH_3$ and $R^3$ is $CH_3$.

6. A process for combatting the growth of unwanted plants as defined in claim 3, wherein in the active compound of the formula Ib, Y is $CH_3$ and $R^3$ is $CH_3$.

7. A compound of the formula Ib as defined in claim 1, wherein Y is $CH_3$ and $R^3$ is $C_2H_5$.

8. A herbicidal composition as defined in claim 2, wherein in the active compound of the formula Ib, Y is $CH_3$ and $R^3$ is $C_2H_5$.

9. A compound of the formula Ib as defined in claim 2, wherein the active compound has the formula Ib, and wherein Y is $CH_3$ and $R^3$ is $C_2H_5$.

10. A compound of the formula Ib as defined in claim 1, wherein Y is $CH_3$ and $R^3$ is n-$C_3H_7$.

11. A herbicidal composition as defined in claim 2, wherein in the active compound of the formula Ib, Y is $CH_3$ and $R^3$ is n-$C_3H_7$.

12. A process for combatting the growth of unwanted plants as defined in claim 3, wherein in the active compound of formula Ib, Y is $CH_3$ and $R^3$ is n-$C_3H_7$.

* * * * *